United States Patent [19]

Williams et al.

[11] 4,110,185
[45] Aug. 29, 1978

[54] IRRADIATION STERILIZATION OF SEMI-CRYSTALLINE POLYMERS

[75] Inventors: Joel Williams, Cary; Terry Dunn; Vivian Stannett, both of Raleigh, all of N.C.

[73] Assignee: Becton, Dickinson and Company, Rutherford, N.J.

[21] Appl. No.: 740,618

[22] Filed: Nov. 10, 1976

[51] Int. Cl.$^2$ .......................... C08F 2/54; C08F 8/18; A61L 1/00; C08J 3/28
[52] U.S. Cl. ................................ 204/159.2; 21/54 R; 128/224; 195/127; 204/159.14; 204/159.18; 250/492 R; 260/45.7 R; 260/45.85 R
[58] Field of Search .................. 21/54 R, 82 R, 82 H; 204/159.18, 159.2, 159.14; 250/492 R

[56] References Cited

U.S. PATENT DOCUMENTS

| | | | |
|---|---|---|---|
| 3,362,897 | 1/1968 | Lawton | 204/159.2 |
| 3,537,967 | 11/1970 | Kelley et al. | 204/159.18 |
| 3,579,303 | 5/1971 | Pickering | 21/54 R UX |
| 3,758,273 | 9/1973 | Johnston et al. | 21/54 R |
| 3,940,325 | 2/1976 | Hirao | 204/159.2 |
| 3,989,611 | 11/1976 | Shurpik | 204/159.18 |

*Primary Examiner*—Barry S. Richman
*Attorney, Agent, or Firm*—Marn & Jangarathis

[57] ABSTRACT

An article of a semi-crystalline polymer such as polypropylene, is sterilized by high energy irradiation, with the polymer containing a non-crystalline mobilizing additive which increases the free volume of the polymer, to thereby prevent embrittlement of the polymer during and subsequent to the irradiation. The additive has a density of from 0.6 to 1.9 g/cm$^3$ and a molecular weight from 100 to 10,000 g/mole.

19 Claims, No Drawings

IRRADIATION STERILIZATION OF SEMI-CRYSTALLINE POLYMERS

This invention relates to the irradiation of polymeric material, and more particularly to irradiation sterilization of polymeric materials.

Semi-crystalline polymeric materials, such as polypropylene, are often employed in articles where it is necessary to subject the article to irradiation sterilization. Such materials, however, degrade during or subsequent to such irradiation; i.e., during shelf storage time, and as a result of such degradation, the articles become embrittled. To date, it has not been generally possible to produce an irradiation sterilized polypropylene article which is not severely limited in its applications as a result of such embrittlement.

An object of the present invention is to provide an irradiation sterilized polymer.

A further object of the invention is to provide an irradiation sterilized polymer which is not embrittled during the irradiation or during storage subsequent to the irradiation.

Another object of the invention is to provide irradiation sterilized articles of polypropylene.

These and other objects of the invention should be apparent from reading the following detailed description thereof.

In accordance with the present invention, there is provided a semicrystalline polymer article which is sterilized by irradiation, with such polymer having incorporated therein during the irradiation a mobilizing amount of a non-crystalline mobilizer.

More particularly, the mobilizer is a low molecular weight noncrystalline substance, which is miscible with the polymeric material and is also compatible therewith; i.e., the mobilizer does not adversely affect the properties of the polymer. The mobilizer is a substance which increases the free volume of the polymer and, therefore, also lowers the density of the polymer. The mobilizer functions to mobilize the amorphous portion of the polymer, and as a result, increases the radical termination reactions which prevent or minimize degradation during and subsequent to the irradiation.

The mobilizer can be any one of a wide variety of liquids which increase the total free volume of the polymer. The term liquid is used herein includes highly viscous substances, commonly referred to as greases. In general, such mobilizers have a density of from 0.6 to 1.9 g/cm$^3$, and preferably of from 0.6 to 1.1 g/cm$^3$. The mobilizer has a low molecular weight, with the average molecular weight, generally being in the order of from 100 to 10,000 grams/mole, and preferably from 100 to 5,000 grams/mole.

As representative examples of suitable mobilizers, there may be mentioned; hydrocarbon oils, halogenated hydrocarbon oils, phthalic ester oils, vegetable oils, silicone oils, low molecular weight non-crystalline polymer greases, such as hydrocarbon polymer greases, low molecular weight polyester greases, polyarylether greases, etc. It is to be understood that the above examples are only illustrative and the use of other mobilizers should be apparent to those skilled in the art from the teachings herein. The preferred mobilizer is a liquid mobilizer which is not highly viscous, and in particular, a hydrocarbon oil or phthalic ester oil.

The polymers employed in the present invention are semi-crystalline polymers, with such polymers having a crystalline content in the order of from 20 to 90, and preferably of from 40% to 80%. The polymer may be comprised of one, two or more monomers, and the term polymer generically refers to both homopolymers and copolymers comprised of two or more monomers. As representative examples of suitable polymers, there may be mentioned: polymers of propylene, ethylene, oxymethylene, butylene, etc. The preferred polymer is polypropylene.

The mobilizer is incorporated into the polymer in a mobilizing amount, with such mobilizer generally being present in an amount of from 0.01% to 50% and preferably of from 0.1% to 20%, all by weight.

The polymer may also include other additives which are conventionally used in the art, such as antioxidants, preservatives, fillers, etc.

Although we do not intend that the present invention be limited by any theoretical reasoning, it is believed that irradiation degrades a polymer, such as polypropylene, by both chain scission and oxidation, as represented by the following equations:

(1) $R \rightarrow R\cdot$ (2) $R\cdot + O_2 \rightarrow RO_2\cdot$ (3) $RO_2\cdot + RH \rightarrow ROOH + R\cdot$ (4) $RO_2\cdot + R\cdot \rightarrow ROOR$ (5) $R\cdot + R\cdot \rightarrow R\text{-}R$ where R represents the long polymeric chain composing the polymer. The ability of steps (2) and (3) to repeat themselves many times before termination by either steps (4) or (5) results in an auto-oxidative reaction. Also, the stability of the radicals formed during irradiation allow this reaction to continue for long periods of time even after radiation has ceased. This post-degradation is very severe since a product can embrittle on the shelf although it was acceptable immediately after irradiation. In accordance with the present invention, it is believed that the presence of the mobilizing additive increases the radical termination reactions shown in steps (4) and (5). Consequently, the oxidative steps (2) and (3) are minimized during irradiation. Equally important, however, the increased termination rates brought about by the mobilizing additive prevent and/or minimize the severe post-oxidative reaction. Therefore, the product does not embrittle during normal shelf time of several years.

The polymer, preferably polypropylene, including the liquid mobilizer can be employed to produce an article which is to be sterilized by procedures known in the art. As representative examples of such articles, there may be mentioned: syringes, tube assemblies, tissue culture flasks, needles, package film, etc.

The polymer having the mobilizer incorporated therein, either as the polymeric material per se, or as an article, e.g., a syringe or package film, can be sterilized by subjecting the polymer to a sterilizing amount of high energy radiation. The high energy radiation can be provided by any one of a variety of sources, including cobalt 60, high energy electrons and X-rays. In general, the sterilizing radiation doses are in the order of from 0.5 to 6 megarads, with the typical dose being 2.5 megarads.

It has been found that by effecting the radiation sterilization of a crystalline polymer having incorporated therein a mobilizer, the sterlized or irradiated polymer is not embrittled, and moreover, does not become embrittled subsequent to the irradiation (no embrittlement with age); i.e., the polymer retains its flexibility. Thus, for example, prior to irradiation, such polymers have a bending angle of at least 90°, and in accordance with the present invention, the irradiated polymer subsequent to irradiation and even after storage for a long period of time has a bending angle of at least 90°.

The invention will be further described with respect to the following examples; however, the scope of the invention is not to be limited thereby.

EXAMPLE 1

Polypropylene containing 4% of an aliphatic hydrocarbon oil having an average molecular weight of 1200 grams/mole (mobilizing additive) was irradiated to 2.5 megarads in air. Following irradiation, the sample could be bent through an angle of 90°. Even after 7 months of aging at ambient conditions, the sample could be bent through an angle 90°. A corresponding control polypropylene sample containing no mobilizing additive was severely embrittled after 2.5 megarads. In fact, this sample only bent 45° before snapping. When this sample was aged for 6 months, it was further embrittled and "snapped" at only a 20° bending angle.

EXAMPLE 2

Polypropylene containing 2% dioctyl phthalate was irradiated (2.5 megarads) in air. Following irradiation the sample was flexible and could bend through an angle of 90°. The irradiated control sample containing no mobilizing additive would only bend through an angle of 20° before snapping.

EXAMPLE 3

Polypropylene containing 3.6% of a hydrocarbon oil as in Example 1 was irradiated to 2.5 megarads in air. Following irradiation the sample was still flexible and would easily bend through an angle of 90° without breaking. A corresponding control sample containing no mobilizing additive was severely embrittled after 2.5 megarads. In fact, the control sample only bent 45° before snapping. When this sample was aged 6 months, it was further embrittled and "snapped" at only a 20° bending angle.

EXAMPLE 4

The polypropylene sample as described in Example 3 except containing 2.4% of a hydrocarbon oil. As in Example 1, the sample was still flexible after 2.5 megarads and would bend through an angle of 90° without breakage.

EXAMPLE 5

The polypropylene sample as described in Example 3 except containing 1.2% of a hydrocarbon oil. As in Example 1, the sample was still flexible after 2.5 megarads and would bend through an angle of 90° without breakage.

The present invention is particularly advantageous in that semicrystalline polymer articles can be irradiation sterilized without detrimentally affecting the flexibility of such articles even after the articles have been stored over a period of time.

Numerous modifications and variations of the present invention are possible in light of the above teachings and, therefore, within the scope of the appended claims, the invention may be practiced otherwise than as particularly described.

What is claimed is:

1. A process for sterilizing a semi-crystalline polymer, comprising:
   subjecting to a sterilizing amount of high energy radiation a semi-crystalline polymer having a crystalline content of from 20-90% and having incorporated therein a mobilizing amount of a non-crystalline liquid mobilizing additive which increases the free volume of the polymer and retains the flexibility thereof to thereby produce a sterilized polymer which retains its flexibility.

2. The process of claim 1 wherein the polymer is in the form of an article.

3. The process of claim 1 wherein the mobilizing additive is miscible with the polymer and has a molecular weight of from 100 to 10,000 grams per mole.

4. The process of claim 3 wherein said mobilizing additive has a density of from 0.6 to 1.9 g/cm$^3$.

5. The process of claim 1 wherein the polymer is polypropylene.

6. The process of claim 5 wherein the mobilizer is a hydrocarbon oil.

7. The process of claim 5 wherein the mobilizing additive is a phthalic ester.

8. The process of claim 1 wherein the mobilizing additive is at least one member selected from the group consisting of hydrocarbon oils, halogenated hydrocarbon oils, phthalic esters, polymer greases, vegetable oils and silicone oils.

9. The process of claim 8 wherein the polymer is polypropylene.

10. The process of claim 9 wherein the mobilizing additive is present in an amount of from 0.1% to 20%, by weight.

11. A flexible sterilized article, comprising: a semi-crystalline polymer having a crystalline content of from 20-90%, said polymer having been irradiated with a sterilizing amount of high energy radiation while having incorporated therein a mobilizing amount of a non-crystalline mobilizing additive which increases the free volume of the polymer and retains the flexibility thereof.

12. The article of claim 11 wherein the mobilizing additive is at least one member selected from the group consisting of hydrocarbon oils, halogenated hydrocarbon oils, phthalic esters, polymmer greases, vegetable oils and silicone oils.

13. The article of claim 12 wherein the polymer is polypropylene.

14. The article of claim 13 wherein said mobilizing additive is present in an amount of from 0.1% to 20%, by weight.

15. The article of claim 11 wherein the mobilizing additive is miscible with the polymer and has a molecular weight of from 100 to 10,000 grams per mole.

16. The article of claim 15 wherein said mobilizing additive has a density of from 0.6 to 1.9 g/cm$^3$.

17. The article of claim 15 wherein the polymer is polypropylene.

18. The article of claim 17 in the form of a syringe.

19. The article of claim 17 in the form of a package film.

* * * * *